United States Patent [19]

Jensen

[11] Patent Number: 5,571,080
[45] Date of Patent: Nov. 5, 1996

[54] SURGICAL DRESSING AND AN ADHESIVE COMPOSITION THEREFOR

[75] Inventor: Ole R. Jensen, 646 Orangeburgh Rd., River Vale, N.J. 07675

[73] Assignee: Ole R. Jensen, Northvale, N.J.

[21] Appl. No.: 223,649

[22] Filed: Apr. 6, 1994

[30] Foreign Application Priority Data

Apr. 20, 1993 [DK] Denmark ................... 0441/93

[51] Int. Cl.⁶ .......................... A61F 13/00; A61F 15/00
[52] U.S. Cl. ..................... 602/56; 602/54; 602/43; 604/307; 604/336
[58] Field of Search ................... 602/41, 44, 53, 602/43, 42, 48, 47, 54, 52, 56, 58, 57; 604/304, 307, 368, 370, 371, 372, 373–375, 337, 308; 128/156; 424/443, 448, 445

[56] References Cited

U.S. PATENT DOCUMENTS

| | | |
|---|---|---|
| 3,339,546 | 9/1967 | Chen . |
| 4,192,785 | 3/1980 | Chen et al. ............ 260/17.4 GC |
| 4,231,369 | 11/1980 | Sorensen et al. . |
| 4,296,745 | 10/1981 | Raymond . |
| 4,367,732 | 1/1983 | Poulsen et al. . |
| 4,551,490 | 11/1985 | Doyle et al. . |
| 4,600,462 | 7/1986 | Watt . |
| 4,738,257 | 4/1988 | Meyer et al. . |
| 4,775,374 | 10/1988 | Cilento et al. ................ 604/344 |
| 4,793,337 | 12/1988 | Freeman et al. ............... 128/156 |
| 4,813,942 | 3/1989 | Alvarez ...................... 604/290 |
| 4,867,748 | 9/1989 | Samuelsen ................... 604/336 |
| 4,909,243 | 3/1990 | Frank et al. .................. 128/156 |
| 5,059,189 | 10/1991 | Cilento et al. ................ 604/307 |

FOREIGN PATENT DOCUMENTS

0343807A2  11/1989  European Pat. Off. ........ A61L 15/06

OTHER PUBLICATIONS

WO92/05755, Apr. 1992 (PCT/US91/06665).

*Primary Examiner*—Randall L. Green
*Assistant Examiner*—Ronald K. Stright, Jr.
*Attorney, Agent, or Firm*—Brinks Hofer Gilson & Lione

[57] ABSTRACT

An adhesive composition, and the surgical dressing of which it is a part, in which the composition takes the form of a water-absorbing and water-swellable hydrocolloid material distributed throughout the interstices of a three-dimensional, open-mesh, randomly-oriented network of flexible, water-insoluble, polymeric filaments, such filaments being surface coated by a tacky, water-insoluble adhesive material that has an adherence affinity for the filaments and that secures such coated filaments together at their points or zones of contact. When hydrated, the hydrocolloid material swells and become a gelatinous continuous phase, with the network of filaments expanding to retain the hydrated hydrocolloid material within the dressing. Despite the phase change, the water-insoluble adhesive material is also retained within the dressing because of its strong adherence to the filaments of the network.

21 Claims, 3 Drawing Sheets

SURGICAL DRESSING AND AN ADHESIVE COMPOSITION THEREFOR

BACKGROUND AND SUMMARY

The present invention relates to the technical field of surgical dressings and adhesive compositions for surgical dressings or skin-adhering devices such as ostomy products, mammary prostheses or any alternative product to be fixated to a skin surface part of a patient or person.

Numerous adhesive compositions known as hydrocolloid compositions or materials are known, e.g. from U.S. Pat. Nos. 3,339,546, 4,192,785, 4,296,745, 4,367,732, 4,813,942, 4,231,369, 4,551,490, 4,296,745, 4,793,337, 4,738,257, 4,867,748, and 5,059,169, to which reference is made and which are hereby incorporated in the present specification by reference.

Conventional hydrocolloid material-containing adhesive compositions comprise a particulate hydrocolloid material such as gelatine, carboxymethylcellulose, and pectin, or mixtures thereof, and a binder or adhesive component which is mixed with the hydrocolloid material in an intimate composition of particulate material in which, following hydration of the hydrocolloid material, the adhesive component constitutes droplets providing adhesion to the skin surface part of the patient or person to whom the surgical dressing or other skin-adhering device is to be adhered by means of the adhesive composition.

It has been realized that the hydrocolloid material-containing adhesive composition has to fulfill certain requirements as to flexibility and cohesion in order to, on the one had render it possible to shape the adhesive composition in conformity with the skin surface part of the patient or person to which skin surface part of the surgical dressing or the skin-adhering device is to be fixated and further to allow any adaptation to changes of the shape of the skin surface part in question and, on the other hand, for preventing components of the adhesive composition, particularly the tacky adhesive component itself, from becoming separated from the major body of the adhesive composition and eventually left at the skin surface part of the patient or person as the surgical dressing or the skin-adhering device is removed from the skin surface part in question.

Where the adhesive composition is part of an adhesive surgical dressing for the treatment of wounds, such as bed sore or pressure sore, the hydrocolloid material-containing adhesive composition further has to exhibit a high liquid- or water-absorbing capability.

In the present context, the term "liquid" means any water-based liquid such as any body fluid, e.g. blood or blood-containing biological liquid, or simply water.

An object of the present invention is to provide an adhesive surgical dressing fulfilling the above requirements as to high flexibility, high cohesion, and high liquid-absorbing capability.

A further object of the present invention is to provide a high flexibility, high cohesion, and high liquid-absorbing adhesive composition for an adhesive surgical dressing, including a skin-adhering device such as an ostomy product, a mammary prosthesis or similar skin-adhering appliance.

A particular advantage of the present invention relates to the fact that the adhesive composition according to the present invention and constituting the adhesive composition of the adhesive surgical dressing according to the present invention exhibits a liquid-absorbing capability in excess of 3 times the weight of the adhesive composition, such as a liquid-absorbing capability of the order of 6–20 times the weight of the adhesive composition, while maintaining its integrity even when highly hydrated, so that such hydrated composition may thereafter be removed substantially intact from a wound and/or from the skin with little if any of the tacky adhesive component remaining as a residue in the wound or on the skin.

A particular feature of the present invention relates to the fact that the adhesive composition according to the present invention and constituting the adhesive composition of the adhesive surgical dressing according to the present invention is easily produced from conventional constituents which in accordance with a novel and surprising realization provides a highly advantageous adhesive composition and highly advantageous adhesive surgical dressing, respectively, exhibiting high flexibility, high cohesion or physical integrity, and a high liquid-absorbing capability.

The above objects, the above advantage, and the above feature together with numerous other objects, advantages, and features which will be evident from the below specification are obtained by means of an adhesive surgical dressing comprising:

a backing layer defining opposite first and second side surfaces, and a adhesive composition applied to said first side surface of said backing layer, said adhesive composition comprising:

a tacky, non-toxic and water-insoluble adhesive material, a hydrocolloid material, and filaments of a substantially elongated configuration, said adhesive material having a strong affinity and providing a surface-coating for said filaments, said filaments and said backing layer being to no substantial extent soluble in said adhesive material, said adhesive-coated filaments defining a three-dimensional mesh structure or network bonded together by said surface-coating of said filaments, and said hydrocolloid material being retained within said mesh structure and being swellable within said mesh structure upon exposure to and absorption of liquid.

It is believed that the adhesive composition of the adhesive surgical dressing according to the present invention acts as a highly-absorbent sponge that resists disintegration and the release of objectionable residue, although the below explanation of the function and operation of the adhesive composition is by no means to be construed as limiting the present invention. It is thus believed that the mesh structure constituted by the filaments which are bonded together through the surface-coating of the filaments provides a sponge network in which the hydrocolloid material, which in an aqueous environment becomes a gel, is retained. As the hydrocolloid particles swell upon exposure to and absorption of water, the cells or interstices of the sponge defined by the mesh structure become enlarged but still remain intact because of the integrity of the filaments which are joined together through the adhesive surface-coating of the filaments.

According to the preferred embodiment of the adhesive surgical dressing according to the present invention, the mesh structure is expandable as the water-swellable hydrocolloid material expands through the absorption of liquid. Thus, the filaments of the mesh structure are in accordance with the preferred embodiment of the adhesive surgical dressing adapted to allow some deformation or rearrangement of the filaments of the three-dimensional mesh structure, still providing a high integrity of the adhesive composition of the adhesive surgical dressing.

The adhesive surgical dressing according to the present invention further preferably exhibits a high liquid-absorbing capability as the adhesive composition is capable of absorbing an amount of water equal to at least 3–6 times the weight of the adhesive composition, preferably an amount of water equal to 6–12 times the weight of the adhesive composition.

It is believed that numerous materials may be used for the flexible, elongated filaments of the adhesive composition which interconnect to provide the three dimensional mesh structure characteristic of the present invention, such as polyethylene, polyesters, polyurethane, or polypropylene. Polyethylene has been found particularly effective but other tough, flexible polymeric materials having similar properties and having an affinity for the adhesive material that coats and joins such filaments together in an open-mesh network are believed suitable.

In accordance with the teachings of the present invention, the filaments may be surface-treated for providing or enhancing such affinity for the adhesive material, e.g. be plasma- or corona-treated or surface-coated by an affinity-promoting agent, such as a binder or adhesive material. Furthermore, the filaments or fibers have to be of adequate strength for providing a three-dimensional mesh structure of adequate strength which may stand the forces which are induced into the mesh structure through the expansion of the hydrocolloid material retained within the mesh structure.

It is believed that the filaments have to constitute a specific minimum amount of the adhesive composition in order to provide an integral mesh structure. Dependent on the filaments, the adhesive material, and the hydrocolloid material in question and further in particular the densities of the materials in question, the filaments are believed to constitute no less than approximately 3%, and preferably no less than approximately 5% by weight of the adhesive composition, in order to provide adequate and sufficient filament material for defining the three-dimensional mesh structure.

The filaments or fibers of the adhesive composition of the adhesive surgical dressing according to the present invention may be made from separate filaments or separate fibers, or alternatively be produced from a film which in accordance with a particular production technique is shredded into elongated filaments. The filaments of the adhesive material of the adhesive surgical dressing according to the present invention are preferably made from a film (or foil) of a thickness of 20–200 μm, such as 20–100 μm, preferably 25–50 μm, defining a major dimension, which major dimension is of the order of 0.5–100 mm, such as 1–10 mm, preferably 1–6 mm. In the present context, the term "major dimension" means a dimension along a predominant direction of a filament in question, as different from e.g. a diameter of sphere. The filaments exhibit a major dimension and further a minor dimension or minor dimensions orientated perpendicularly to the major dimensions.

Alternatively, the filaments may constitute fibers defining a length and a diameter, which length and which diameter are of the order of 5–100 mm and 5–50 μm, respectively, such as 6–60 mm and 10–30 μm, respectively, preferably approx. 3–40 mm and approx. 21 μm (3.3 dTex), respectively. The tacky adhesive material of the adhesive composition of an adhesive surgical dressing embodying the present invention may be made from any of numerous viscous, water-insoluble gum-like materials such as polyisobutylene, silicone rubbers, polyurethane rubber, sucrose acetate isobutylate, acrylonitrile rubber, butyl rubber, natural or synthetic gum or rubber-like materials optionally in combination with plasticizers, tackifiers or solvents enhancing the adhesive characteristics of said materials, or mixtures thereof.

The hydrocolloid material of the adhesive composition of the adhesive surgical dressing according to the present invention may constitute a water-absorbing and/or water-swellable material such as carboxymethylcellulose, carboxymethyl starches, and alkali metal derivatives thereof, alginates, polyvinyl alcohol, carrageenan, gelatine, citrus pectin, powdered pectin, synthetic or natural gums, such as gum guar, gum arabic, locust bean gum, karaya, or mixtures thereof.

The hydrocolloid material may be a liquid or a solid material but would normally be present in the adhesive composition in particulate or finely divided form. When the hydrocolloid material is exposed to aqueous liquid, such hydrocolloid material swells and provides in most instances a gel which is retained within the three-dimensional mesh structure defined by the filaments of the adhesive composition.

The backing layer of the adhesive surgical dressing according to the present invention may be made from a water-and/or air-permeable material, or alternatively a water-and/or air-impermeable material, or a combination of such materials, e.g. a laminated structure including permeable and impermeable materials. The adhesive composition may be adhered through its adhesive component to the backing layer and, alternatively, may be adhered to the backing layer through a tie layer constituted by a glue layer or an adhesive layer, such as an acrylic binder layer.

The backing layer may be made from any appropriate plastic film material such as polyurethane, polyethylene, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, or mixtures thereof, although an elastomeric backing composed of a thin, stretchable film of polyurethane or similar material is preferred.

According to preferred embodiments of the adhesive surgical dressing, the adhesive composition comprises polyisobutylene in an amount of 30–56%, such as 40–60%, e.g. or preferably 42%, 44% or 60%, by weight of said adhesive composition.

According to preferred embodiments of the adhesive surgical dressing according to the present invention, the adhesive composition comprises particles of hydrocolloid material composed of gelatine, carboxymethyl cellulose and pectin in a total amount of 8–65%, such as 35–50%, e.g. or preferably 48% or 25% by weight of said adhesive composition.

According to preferred embodiments of the adhesive surgical dressing according to the present invention, the adhesive composition comprises filaments made from polyethylene in an amount of 3–25%, such as 5–15%, e.g. or preferably 10%, 8% or 15%, respectively, by weight of said adhesive composition.

The above objects, the above advantage, and the above feature, together with numerous other objects, advantages, and features which will be evident from the present specification, are obtained by means of an adhesive composition for the fixation of an ostomy product or similar product to a skin surface part of a patient or person, said adhesive composition comprising:

a non-toxic and water-insoluble tacky adhesive material, a water absorbing and swellable hydrocolloid material, and a multiplicity of randomly-oriented polymeric filaments coated by said adhesive material and secured together at points of intersection by said adhesive material to define a three-dimensional open-mesh network, said hydrocolloid material being retained within said mesh network and being expandable within the openings of said mesh network through the absorption of aqueous liquid.

The adhesive composition according to the present invention, may advantageously comprise any of the characteristics of the adhesive composition of the adhesive surgical dressing according to the present invention.

DRAWINGS

Figure 1:
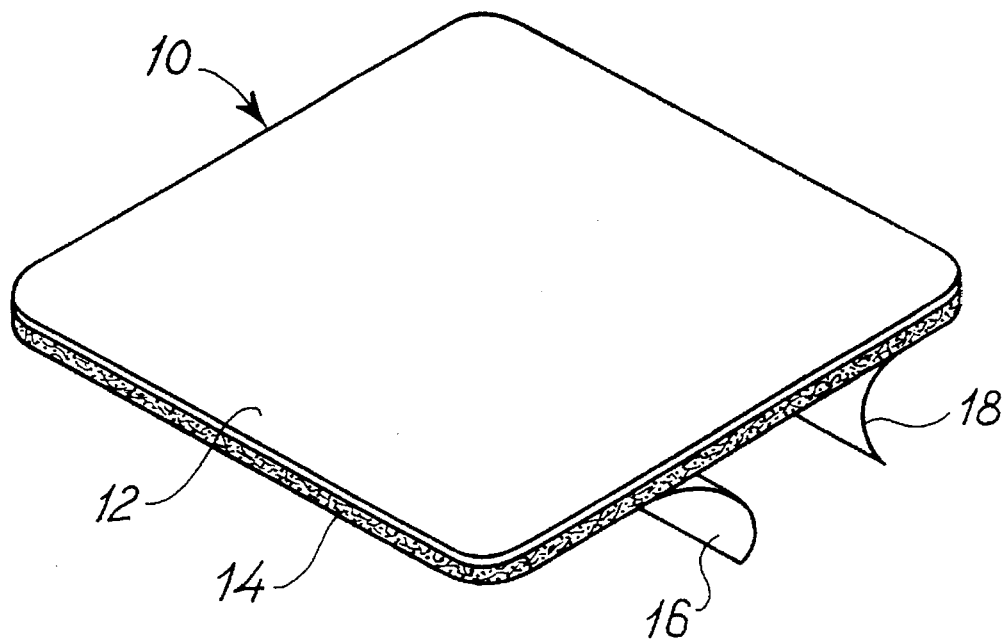
FIG. 1 is a perspective view of a first and presently preferred embodiment of an adhesive surgical dressing according to the present invention, disclosing an outer side surface of the adhesive surgical dressing.
Figure 2:
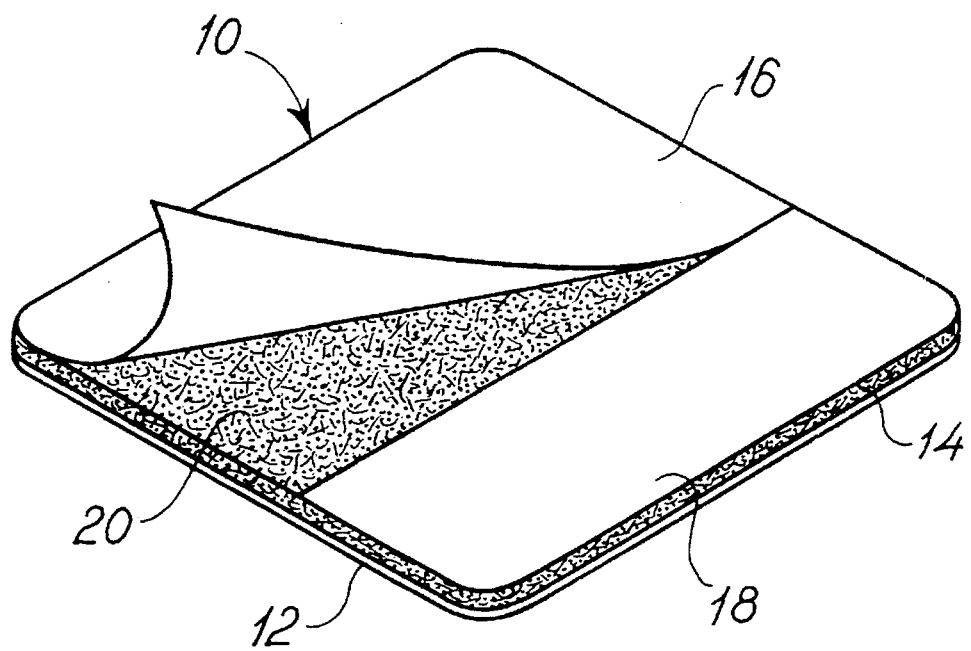
FIG. 2 is a perspective view of the first embodiment of the adhesive surgical dressing also shown in FIG. 1, disclosing release sheet parts of the dressing and an adhering side surface to be arranged in contact with a skin surface part of a patient or person.
Figure 8:
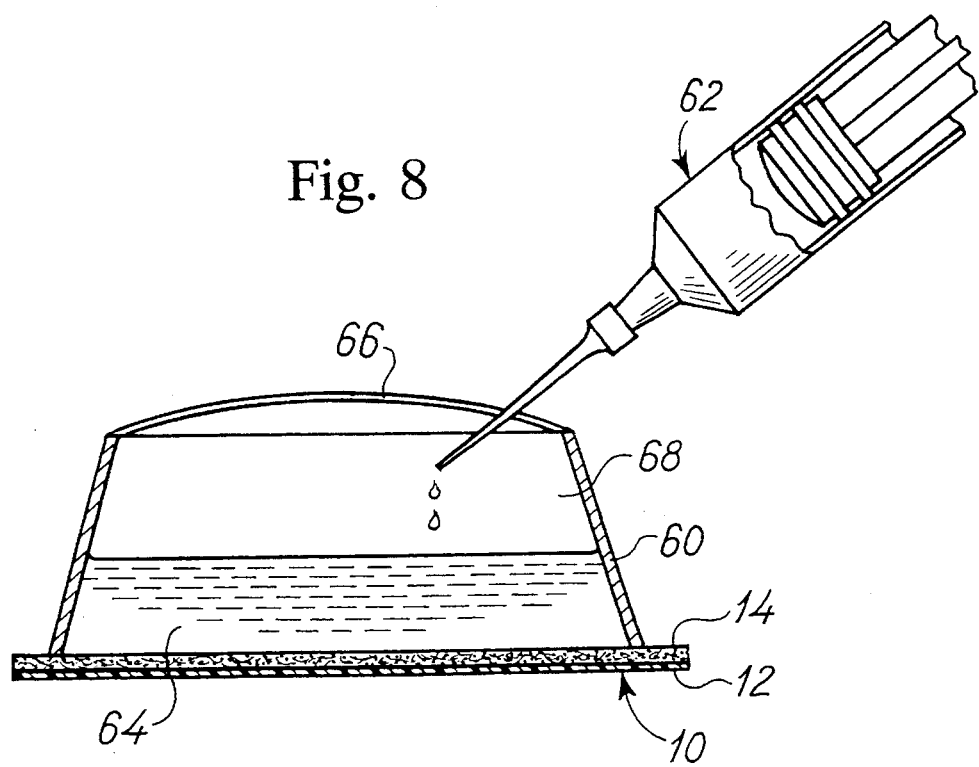
Figure 9:
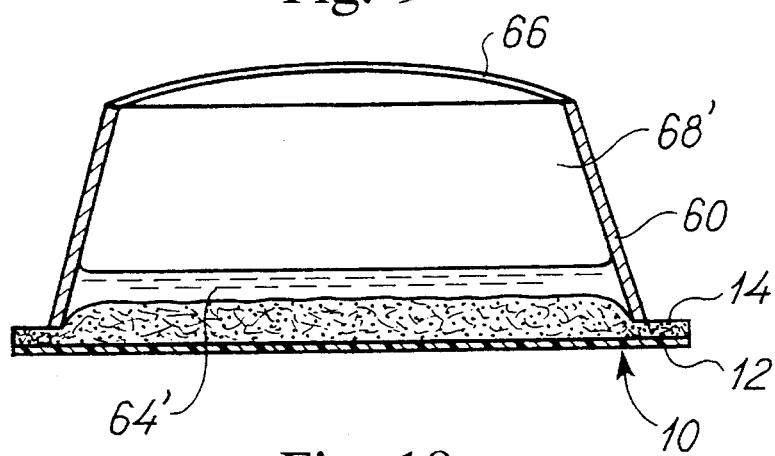
Figure 10:
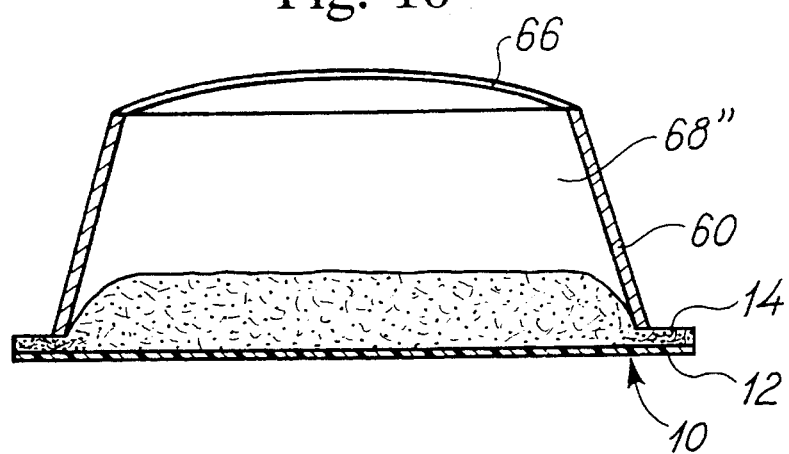

FIGS. 8, 9, and 10 are schematic views of a testing procedure through which the water-absorbing capability of the adhesive surgical dressing shown in FIGS. 1 and 2 is demonstrated.

DETAILED DESCRIPTION OF PREFERRED EMBODIMENTS

In FIGS. 1 and 2, a first embodiment of an adhesive surgical dressing according to the present invention is shown, generally designated by the reference number 10. The adhesive surgical dressing 10 is of a structure adapted to be adhered to a skin surface of a patient over and about a wound area such as, for example, a pressure sore or bed sore. Like conventional adhesive surgical dressings to be applied for the treatment of pressure sores or other types of wounds, the adhesive surgical dressing 10 according to the present invention is adapted to absorb fluids from the wound while at the same time protecting the wound from contaminating or irritating agents and elements.

The adhesive surgical dressing 10 comprises a backing layer 12 of foil or film serving the purpose of supporting a layer of an adhesive composition 14 applied to a surface of the backing layer 12. The adhesive composition 14 may be applied and adhered directly to the backing layer 12 or a tie layer (not shown) such as a glue or adhesive layer may be interposed between the other two layers. The surface of the backing layer 12 opposite from the surface to which the adhesive composition is applied constitutes the external surface relative to the site of application of the adhesive surgical dressing 10. In FIG. 2, the opposite wound-facing surface 20 of the adhesive surgical dressing 10 is shown. Two paper release sheets 16 and 18 cover surface 20 until the dressing is used, at which time they are peeled away to expose surface 20 as indicated. The backing layer 12 may be made from any appropriate polymeric film (foil) material, such as a thin film of polyethylene, polyurethane, or other thin, flexible plastic material. An elastomeric film such as polyurethane is believed particularly desirable. The backing layer 12 may in accordance with alternative embodiments constitute a liquid- and/or air-permeable film (foil) or membrane, or alternatively a liquid- and/or air-permeable film or membrane.

The adhesive composition 14, in accordance with the teachings of the present invention as implemented in the below examples, is comprised of an adhesive composition fulfilling the main characteristics of adhesive compositions sought in connection with adhesive surgical dressings, viz. the characteristics or requirements of high liquid absorption capability, high flexibility, biocompatability, and resistance to disintegration even when fully swollen or hydrated, with minimal release or liberation of those constituents that may not be readily (and safely) absorbed by the body. The adhesive composition according to the present invention constitutes an integral structure in which a mesh network of polymeric filaments or fibers are held together by a tacky binder or adhesive material in which the network restrains the liquid-absorbing (hydrocolloid) material from being liberated and the strong affinity between the polymeric network and the adhesive material effectively prevents most, if not all, of such adhesive material from being liberated under conditions of use.

The adhesive composition according to the present invention further in accordance with the presently preferred embodiment of the adhesive composition allows the absorption of an amount of water amounting to 6–20 times the weight of the adhesive composition.

Figure 3:
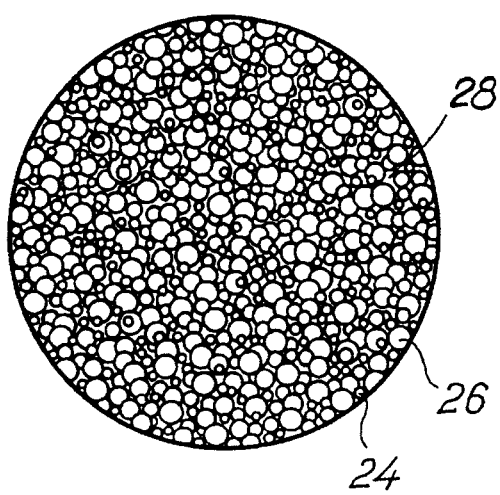
FIG. 3 is a somewhat schematic microscopic view of a conventional adhesive compound.

FIG. 3 is a microscopic view showing a conventional hydrocolloid-containing adhesive composition after fluid absorption has resulted in phase conversion. Prior to hydration, the hydrocolloid content ordinarily takes the form of solid particles (the discontinuous phase) dispersed in a matrix of a semi-fluid adhesive material such as polyisobutylene (the continuous phase). In use of the dressing, the hydrocolloids absorb aqueous fluid and swell to become the continuous phase with the water-insoluble adhesive material breaking up into droplets distributed throughout the continuous hydrocolloid gel. FIG. 3 therefore depicts droplets 24, 26 of varying size of adhesive material dispersed throughout the continuous hydrocolloid matrix 28. Upon removal of such a dressing from a wound site, some of the adhesive droplets, being in the form of discrete particles distributed throughout an aqueous gel, are free to leave the dressing and remain as a insoluble residue in and about the wound.

Figure 4:
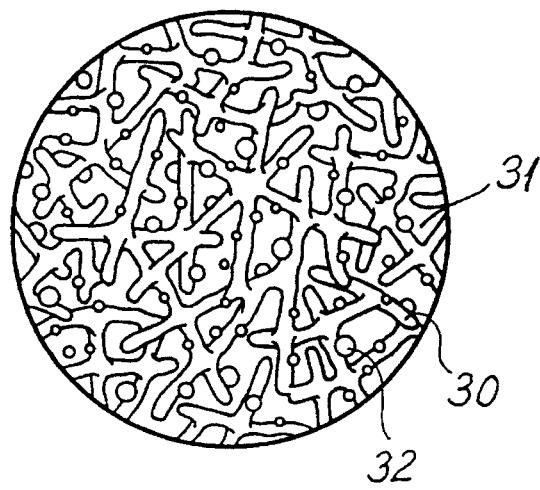
FIG. 4 is a somewhat schematic microscopic view similar to the view of FIG. 3, illustrating a preferred embodiment of an adhesive compound according to the present invention.

FIG. 4 is a microscopic view depicting the adhesive composition of this invention under similar conditions approaching full hydration. Although a phase change has occurred, the adhesive material (polyisobutylene) is immobilized as a coating upon the filaments of polyethylene. The coated filaments 30 extend randomly in different directions, forming a three-dimensional network having the sponge-like appearance of a reticulated polymeric foam. Because of the strong affinity between the adhesive material and the polymeric filaments, the network of filaments immobilizes the adhesive material and the adhesive in turn functions as a connecting agent to secure the filaments together at their points of contact and thereby maintain the integrity of the open-celled network. The hydrated hydrocolloid 31 extends throughout the interstices of the filamentary network as the hydrated continuous phase although some hydrocolloid that is not yet fully hydrated, or has lower capacity for liquid absorption than other hydrocolloid constituents, may still appear in the form of distinguishable particles 32. It should be noted that under the conditions illustrated in FIG. 4, a hydrocolloid constituent such as carboxymethylcellulose, which is known for its liquid-absorbing activity and capacity, is already in a gel state and, because of its swollen condition, is entrapped within the spaces or interstices of the coated fiberous network. As a result, when a dressing having the adhesive composition of this invention becomes hydrated by wound exudate and is removed from a wound site for inspection or dressing replacement, it has been found that such a dressing may be removed intact with essentially none of the adhesive material remaining in the wound and with most, if not all, of the carboxymethylcellulose being entrapped in the network of the removed dressing.

It is important that there be an affinity between the tacky adhesive material of the composition and the polymeric fibers that make up the restraining network and, further, that the adhesive material be water insoluble. It has been known to add fibrous filler materials, such as fibers of cotton or rayon (viscose), to adhesive compositions to serve as strengthening agents, but such fibers do not coact with an adhesive material such as polyisobutylene to produce a coated network of filaments capable of achieving the results described herein.

Figure 5:
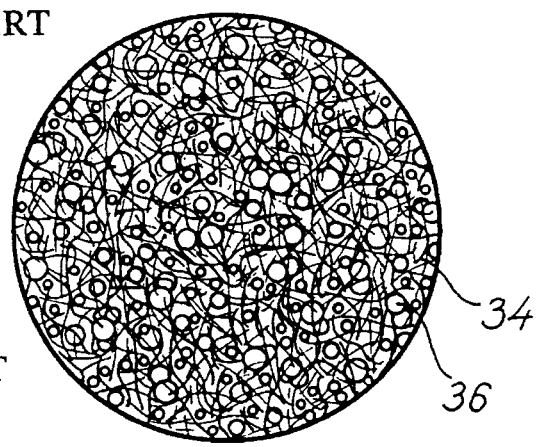
FIG. 5 is a somewhat schematic microscopic view similar to the views of FIGS. 3 and 4, illustrating a further conventional adhesive compound.

FIG. 5 is a microscopic view of a conventional adhesive composition that is similar to the composition of FIG. 3 but additionally contains a filler of viscose fibers 34. The adhesive material remains in the form of droplets 36 similar to the droplets 26 of FIG. 3. The viscose fibers are neither coated nor interlocked by the adhesive material, with the result that the composition of FIG. 5, like that of FIG. 3, suffers from the serious drawbacks that the adhesive particles may be liberated and are free to migrate into a wound as the hydrocolloids absorb exudate and cause the adhesive composition and the dressing as a whole to expand. Since the adhesive material (e.g. polyisobutylene) is not immobilized by the fibrous filler, and since the fibers of the filler material are not interconnected by the adhesive but are free to be released from the dressing, both fibers and adhesive particles may be left at a wound site when such a dressing is removed. Such problems are of course increased if such a dressing disintegrates upon removal, a not-infrequent experience with prior dressings.

Figure 6:
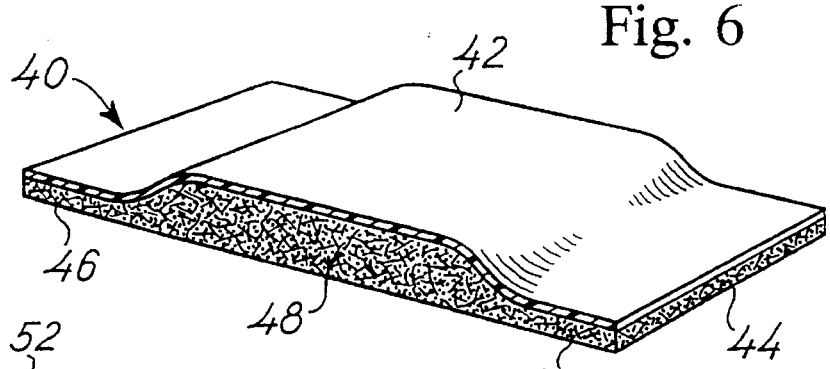
FIG. 6 is a schematic, sectional and perspective view of a second embodiment of an adhesive surgical dressing according to the present invention.
Figure 7:
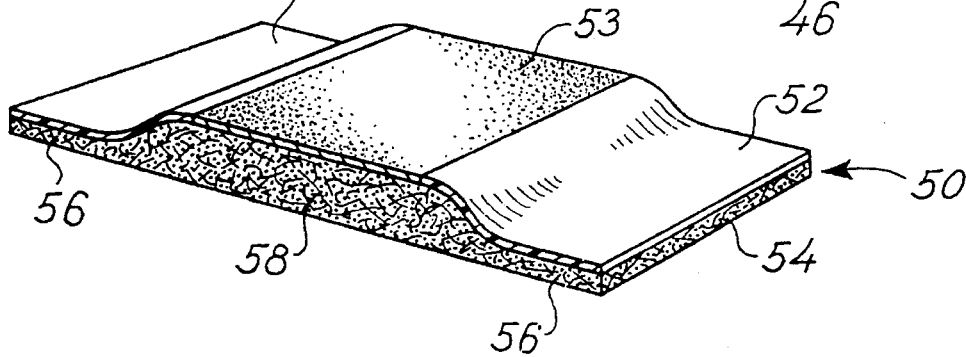
FIG. 7 is a schematic, sectional and perspective view similar to the view of FIG. 6 of a third embodiment of an adhesive surgical dressing according to the present invention.

In FIGS. 6 and 7, alternative embodiments of the adhesive surgical dressing according to the present invention are shown. In FIG. 6, a second embodiment is shown, generally designated by reference numeral 40. Similar to the first embodiment described above with reference to FIGS. 1 and 2, the second embodiment 40 comprises a backing layer 42 to which an adhesive composition 44 according to the present invention is adhered, optionally through a tie layer, such as a glue or adhesive layer. The adhesive composition 44 defines three segments of varying thickness, viz. a central, fairly thick segment or area designated the reference number 48 and two shallow rim segments designated the reference number 46. The surgical dressing 40 is basically of a structure similar to the occlusive wound-care dressing described in U.S. Pat. No. 4,738,257, to which reference is made, and which patent is hereby incorporated in the present specification by reference.

In FIG. 7, a third embodiment of the adhesive surgical dressing according to the present invention is shown, generally designated by reference numeral 50. The third embodiment shown in FIG. 7 differs from the second embodiment shown in FIG. 6 in that the backing layer of FIG. 6, which constitutes a continuous film or foil, is replaced by three film or foil segments comprising two rim segments 52 and a central segment 53. The backing layer assembly comprising the rim segments 52 and the central segment 53 is adhered to an adhesive composition 54 similar to the adhesive composition 44 and includes rim segments 56 and a central segment 58 corresponding to the rim segments 46 and the central segment 48, respectively, of FIG. 6.

In FIGS. 8, 9, and 10, a testing routine is illustrated, which testing routine demonstrates the highly advantageous water-absorbing capability of the adhesive composition of the adhesive surgical dressing 10 described above with reference to FIGS. 1 and 2. In FIG. 8, the adhesive surgical dressing 10 is arranged upside-down as the exposed adhering surface 20 of the adhesive composition 14 is facing upwardly. On top of the exposed adhering surface 20 is positioned a cup 60 having an air-permeable mesh segment 66. By means of a syringe 62, an amount of water of a total weight corresponding to 6–8 times the weight of the adhesive composition of the adhesive surgical dressing 10 is introduced into the interior of the cup 60. The water introduced into the interior of the cup 60 is designated by the reference numeral 64 and the reference numeral 68 designates an air space above the upper surface of the water 64 within cup 60.

After a period of time, such as 24 hours, a major part of the water has been absorbed by the adhesive composition including swellable hydrocolloid material of the adhesive surgical dressing 10. FIG. 9 illustrates the situation after approximately 24 hours, revealing by comparison with FIG. 8 that a major part of the water has been absorbed by the hydrocolloid material of the adhesive composition of the adhesive surgical dressing 10, reducing the remaining amount of free water, which amount is designated the reference numeral 64'. The reference numeral 68' designates the air space above the surface of the water 64' within the cup 60.

After a further 48 hour period, water originally introduced into the interior of the cup 60 has been totally absorbed by the now greatly swollen hydrocolloid material of the adhesive composition of dressing 10, as is illustrated in FIG. 10. The thickness of the adhesive composition 14 of the dressing 10 has been increased by a factor of 6 to 8 as compared to the thickness of the adhesive composition 14 shown in FIG. 8. Reference numeral 68" designates the air space defined above the exposed dry surface of the adhesive composition 14 of the adhesive dressing 10.

The following examples are further illustrative of the present invention.

EXAMPLE 1

This example is directed to the preparation of 100 kg adhesive composition according to a first and presently preferred embodiment of the adhesive composition according to the present invention. Polyisobutylene (PIB), 44% (w/w), was added to a Sigma Blade Mixer, with stirring, heated to approx. 50° C. After 2–5 min. a hydrocolloid mixture of gelatine-carboxymethylcellulose-pectin (1:1:1), 48% (w/w), was added in 3 portions, and simultaneously a polyethylene foil (film) was added, 8% (w/w), having a thickness of approx. 25–50 μm. During the mixing procedure which lasted approximately 30 min., the foil (film) was shredded into filaments and the hydrocolloid mixture was divided into particulate form. The temperature of the mixture was monitored continuously, and when the mixture reached 65° C., cooling of the mixer was initiated. The mixing procedure was continued until visual uniformity was obtained after approx. 1–1.5 hours, thereby providing an adhesive composition including polyethylene filaments having a length of approx. 1–6 mm and defining a mesh structure for retaining a particulate hydrocolloid mixture.

EXAMPLE 2

In accordance with the procedure of Example 1, a second embodiment of the adhesive composition according to the present invention was produced, using 60% (w/w) of PIB, 25% (w/w) of hydrocolloid mixture, and 15% (w/w) of polyethylene foil (film), respectively.

EXAMPLE 3

In accordance with the procedure of Example 1, a third embodiment of the adhesive composition according to the present invention was produced, using 42% (w/w) of PIB, 48% (w/w) of hydrocolloid mixture, and 10% (w/w) of polyethylene foil (film), respectively.

EXAMPLE 4

The adhesive surgical dressing shown in FIGS. 1 and 2 was produced as follows:

To one side surface of a continuous polyurethane foil (film) of a thickness of approx. 25 μm the adhesive composition of Example 1 was applied as a continuous layer of a thickness of approx. 1.5 mm. The adhesive composition was adhered to the polyurethane foil (film) through an acrylic binder constituting an adhering layer. The thus produced composite foil assembly was cut into 10×10 cm squares constituting individual adhesive surgical dressings.

EXAMPLE 5

This example is directed to the preparation of 100 kg adhesive composition according to a first and present preferred embodiment of the adhesive composition according to the present invention. Polyisobutylene (PIB), 44% (w/w), was added to a Sigma Blade Mixer, with stirring, heated to approx. 50° C. After 2–5 min. a hydrocolloid mixture of gelatine-carboxymethylcellulose-pectin (1:1:1), 48% (w/w), was added in 3 portions, and simultaneously polyethylene fibers were added, 8% (w/w), having a diameter of approx. 21 μm (3.3 dTex) and a length of approximately 40 mm. During the mixing procedure which lasted approximately 30 min., the hydrocolloid mixture was divided into particulate form. The temperature of the mixture was monitored continuously, and when the mixture reached 65° C., cooling of the mixer was initiated. The mixing procedure was continued until visual uniformity was obtained after approx. 1–1.5 hours, thereby providing an adhesive composition including polyethylene fibers defining a mesh structure for retaining the particulate hydrocolloid mixture.

EXAMPLE 6

In Example 5, polyester and polypropylene may be used as alternative fiber materials. Other fiber materials having affinity to the adhesive material may also be relevant.

EXAMPLE 7

A solubility test was performed to identify those materials that were extractable by a saline solution from an adhesive composition made in accordance with Example 1. A sample of the adhesive composition (2.2293g) was immersed in 100 ml of 0.9% NaCl solution and was maintained at 37° C. for 66 hours. After the soaking period, the saline solution was evaporated to dryness. The dried material was suspended in 30 ml deionized water and shaken vigorously. The suspension was centerfuged, yielding a clear solution and a gel at the base of the tube.

Infrared spectra of all the individual components and the extract fractions were acquired to identify materials in the extract. Neither polyisobutylene nor polyethylene were detected in the extract as revealed by the absence of characteristic peaks for those polymers in the extract spectrum. The spectrum of the extract was found to be complex and comparison with the spectra of the individual components revealed that the extract is not simply one of such components. However, further observations revealed that the spectrum of the extract could be accounted for almost entirely by assuming the extract contained only pectin and gelatin. Thus, a synthetic spectrum produced by adding together the individual spectra of gelatin and pectin was in excellent agreement with the observed spectrum of the extract. While only pectin and gelatin could be detected in the extract, it was originally thought a minor component in the extract might possibly be carboxymethylcellulose (CMC). While it is possible that trace amounts of CMC were extracted along with the gelatin and pectin, the amounts, if any, were so slight that the presence of CMC in the abstract was beyond the sensitivity of the test.

While in the forgoing, embodiments of the invention have been disclosed in considerable detail for purposes of illustration, it will be understood by those skilled in the art that many of these details may be varied without departing from the spirit and scope of the invention.

I claim:

1. An adhesive surgical dressing comprising:

a backing layer having first and second side surfaces, and an adhesive composition applied to one of said surfaces;

said adhesive composition comprising a three-dimensional, open cell mesh network of discrete polymeric filaments coated with a tacky water-insoluble adhesive material having an adherence affinity for said filaments and joining the coated filaments together at their intersections to maintain the integrity of said said network;

and a hydrocolloid material composed of one or more water-absorbing and swellable hydrocolloids, said hydrocolloid material being dispersed throughout the open cells of said network;

said network being expandable for retaining said hydrocolloid material when said hydrocolloid material absorbs water and swells as it becomes hydrated, said filaments constituting no less than 3% by weight of said adhesive composition.

2. The dressing of claim 1 in which said hydrocolloid material comprises one or more hydrocolloids selected from the group consisting of carboxymethyl cellulose, carboxymethyl starches, and alkali metal derivatives thereof, alginates, polyvinyl alcohol, carrageenan, gelatine, pectin, gum guar, gum arabic, locust bean gum, and karaya.

3. The dressing of claim 2 in which said hydrocolloid material is present in said composition in the form of particles.

4. The dressing of claim 1 in which said filaments are formed of a polymeric material selected from the group consisting of polyethylene, polypropylene, polyesters, and polyurethane.

5. The dressing of claim 1 in which said filaments constitute no less than approximately 5% by weight of said adhesive composition.

6. The dressing of claim 1 in which each of said filaments has a length of within the range of 5 to 100 mm and a diameter within the range of about 5 to 50 μm.

7. The dressing of claim 1 in which said adhesive material is selected from the group consisting of polyisobutylene, silicone rubbers, polyurethane, sucrose acetate isobutylate, acrylonitrile rubber, butyl rubber, natural or synthetic rubber materials optionally in combination with plasticizers, tackifiers or solvents enhancing the adhesive characteristic of said adhesive material.

8. The dressing of claim 1 in which said backing layer comprises a thin film of polymeric material selected from the group consisting of polyurethane, polypropylene, styrene-isoprene copolymers, styrene-butadiene block copolymers, butadiene rubbers, isoprene rubbers, neoprene rubbers, acrylonitrile rubbers, silicone rubbers, butyl rubbers, chloroprene rubbers, polyvinylchloride, polyamides, or mixtures thereof.

9. The dressing of claim 1 in which said adhesive material comprises polyisobutylene in an amount within the range of 30–65% by weight of said adhesive composition.

10. The dressing of claim 1 in which said hydrocolloid material comprises a mixture of gelatine, carboxymethyl cellulose and pectin within the range of about 8–65% by weight of said composition.

11. The dressing of claim 1 in which the polymer of said filaments is polyethylene in an amount within the range of 3–25% by weight of said adhesive composition.

12. An adhesive composition for securing a surgical dressing to a patient's skin, said composition comprising:

a three-dimensional, open cell mesh network of discrete polymeric filaments coated with a tacky water-insoluble adhesive material having an adherence affinity for said filaments and joining the coated filaments together at their intersections to maintain the integrity of said network; and a hydrocolloid material composed of one or more water-absorbing and swellable hydrocolloids, said hydrocolloid material being dispersed throughout the open cells of said network;

said network being expandable for retaining said hydrocolloid material when said hydrocolloid material absorbs water and swells as it becomes hydrated, said filaments constituting no less than 3% by weight of said adhesive composition.

13. The composition of claim 12 in which said hydrocolloid material comprises one or more hydrocolloids selected from the group consisting of carboxymethyl cellulose, carboxymethyl starches, and alkali metal derivatives thereof, alginates, polyvinyl alcohol, carrageenan, gelatine, pectin, gum guar, gum arabic, locust bean gum, and karaya.

14. The composition of claim 13 in which said hydrocolloid material is present in said composition in the form of particles.

15. The composition of claim 14 in which said filaments are formed of a polymeric material selected from the group consisting of polyethylene, polypropylene, polyesters, and polyurethane.

16. The composition of claim 12 in which said filaments constitute no less than approximately 5% by weight of said adhesive composition.

17. The composition of claim 12 in which each of said filaments has a length of within the range of 5 to 100 mm and a diameter within the range of about 5 to 50 μm.

18. The composition of claim 12 in which said adhesive material is selected from the group consisting of polyisobutylene, silicone rubbers, polyurethane, sucrose acetate isobutylate, acrylonitrile rubber, butyl rubber, natural or synthetic rubber materials optionally in combination with plasticizers, tackifiers or solvents enhancing the adhesive characteristic of said adhesive material.

19. The composition of claim 12 in which said adhesive material comprises polyisobutylene in an amount within the range of 30–65% by weight of said adhesive composition.

20. The composition of claim 12 in which said hydrocolloid material comprises a mixture of gelatine, carboxymethyl cellulose and pectin within the range of about 8–65% by weight of said composition.

21. The composition of claim 12 in which the polymer of said filaments is polyethylene in an amount within the range of 3–25% by weight of said adhesive composition.

* * * * *